(12) United States Patent
Kojima

(10) Patent No.: US 7,582,795 B2
(45) Date of Patent: Sep. 1, 2009

(54) APPARATUS FOR SYNTHESIZING UREA AND METHOD FOR REVAMPING THE SAME

(75) Inventor: Yasuhiko Kojima, Narashino (JP)

(73) Assignee: Toyo Engineering Corporation, Tokyo (JP)

( * ) Notice: Subject to any disclaimer, the term of this patent is extended or adjusted under 35 U.S.C. 154(b) by 143 days.

(21) Appl. No.: 11/909,765

(22) PCT Filed: Apr. 24, 2006

(86) PCT No.: PCT/JP2006/308529

§ 371 (c)(1),
(2), (4) Date: Sep. 26, 2007

(87) PCT Pub. No.: WO2006/118071

PCT Pub. Date: Nov. 9, 2006

(65) Prior Publication Data

US 2009/0062566 A1    Mar. 5, 2009

(30) Foreign Application Priority Data

Apr. 27, 2005 (JP) ............................. 2005-129880

(51) Int. Cl.
*C07C 273/04* (2006.01)
*B01J 8/04* (2006.01)

(52) U.S. Cl. .............................. 564/68; 564/67; 564/69; 564/70; 564/71; 564/72; 422/188; 422/189; 422/190; 422/191; 422/192; 422/193; 422/194; 422/195

(58) Field of Classification Search .................... 564/87, 564/569, 70, 71, 72; 422/188, 189, 190, 422/191, 192, 193, 194, 195
See application file for complete search history.

(56) References Cited

U.S. PATENT DOCUMENTS 5,936,122 A    8/1999    Kojima et al.
6,093,850 A    7/2000    Kojima et al.
6,518,457 B1   2/2003    Sakata et al.
2002/0004612 A1 1/2002   Fukunaka et al.
2002/0082451 A1 6/2002   Yoshida et al.

FOREIGN PATENT DOCUMENTS

| JP | 59-122452 | 7/1984 |
|----|-----------|--------|
| JP | 10-120643 | 5/1998 |
| JP | 10-182586 | 7/1998 |
| JP | 10-182587 | 7/1998 |
| JP | 11-180942 | 7/1999 |
| JP | 2002-20360 | 1/2002 |
| JP | 2002-145850 | 5/2002 |
| JP | 2003-104949 | 4/2003 |
| WO | WO 00/00466 | 1/2000 |
| WO | WO 00/43358 | 7/2000 |
| WO | WO 01/72700 A1 | 10/2001 |

*Primary Examiner*—Peter G O'Sullivan
(74) *Attorney, Agent, or Firm*—Knobbe Martens Olson & Bear LLP

(57) ABSTRACT

It is intended to enable an apparatus for synthesizing urea and a method for revamping the same to place a heavy condenser at a relatively low position and to circumvent problems associated with letting a process fluid flow within a tube in the condenser. The present invention provides an apparatus for synthesizing urea including: a synthesis reactor for reacting $NH_3$ with $CO_2$ to obtain a urea synthesis solution containing urea, unreacted $NH_3$ and $CO_2$, and water; a stripper for stripping the urea synthesis solution with use of at least a part of raw material $CO_2$ to separate a gas containing the unreacted $NH_3$ and $CO_2$; a vertical submerged condenser having a shell and tube structure for condensing the gas in an absorbing medium on the shell side while cooling the gas with a cooling medium passing through the tube side; and recycling means for recycling a liquid obtained from this condenser to the synthesis reactor, wherein this condenser is placed below the synthesis reactor. The present invention also provides a method for revamping an apparatus for synthesizing urea having a synthesis reactor, including installing the apparatus with the stripper, the vertical submerged condenser, and the recycling means, wherein this condenser is placed below the synthesis reactor.

18 Claims, 6 Drawing Sheets

APPARATUS FOR SYNTHESIZING UREA AND METHOD FOR REVAMPING THE SAME

TECHNICAL FIELD

The present invention relates to an apparatus for synthesizing urea that synthesizes urea by using ammonia and carbon dioxide as raw materials. To be more specific, the present invention relates to an apparatus used in a stripping urea process wherein a urea synthesis solution obtained in a synthesis reactor for synthesizing urea is stripped.

BACKGROUND ART

Techniques as described below are known as to a stripping urea process.

Patent Document 1 has described a urea process using ammonia and carbon dioxide as raw materials, wherein urea synthesis is effected wholly or partly in a combi-reactor. In this process disclosed therein, a gas from a stripper is supplied to the vertical combi-reactor and condensed wholly or partially in ammonium carbamate, which is in turn transferred from a scrubber zone to a condensation section via a downcomer, and ammonia and carbon dioxide are partially synthesized into urea in the condensation zone of the combi-reactor while the further conversion to urea is conducted in the reaction zone of the combi-reactor.

Patent Document 2 has described a combined reactor installation using ammonia and carbon dioxide as raw materials, which is composed of two vertically installed synthesis zones and one condensation zone. This installation is a vertical combined reactor in which two reaction zones are separated by a high-pressure condensation zone. The document has also disclosed another combined reactor including two reaction zones and a high-pressure condensation zone placed outside the reactor, and has further disclosed a process using this installation. Moreover, a method involving wholly or partly feeding a gas supplied from a stripper to the high-pressure condensation zone has also been disclosed therein. In the disclosure, it is preferred that the gas from the stripper is supplied via an ammonia ejector to the second reaction zone in the vertically installed combined reactor.

Patent Document 3 has described an improving method capable of placing an apparatus on the ground in a synthesis method of urea including a stripping step of unreacted ammonia and carbon dioxide at a pressure nearly equal to the pressure of urea synthesis by raw material carbon dioxide and a condensation step of a gas mixture from the stripping step. In this synthesis method of urea disclosed therein, a vertical condenser for bringing a gas mixture from a stripper into contact with an absorbing medium under cooling and thereby condensing the gas mixture is provided above a urea synthesizing tower, and a first down pipe for communicating the top of the condenser to the bottom of the synthesizing tower is provided, whereby the produced condensed liquid is made to flow to the bottom of the synthesizing tower by gravity and then subjected to urea synthesis together with a part of raw material ammonia or carbon dioxide fed thereto, and the produced urea synthesis solution is introduced through a second down pipe having an opening in the top of the synthesizing tower into the stripper by gravity, in which unreacted ammonia and carbon dioxide are then separated as the gas mixture by the remainder of raw material carbon dioxide, then introduced to the bottom of the condenser, and condensed, or alternatively, a condensed liquid from the vertical condenser is sucked by an ejector using preheated raw material ammonia as a driving fluid, then introduced into the bottom of the urea synthesizing tower, and subjected to urea synthesis.

Patent Document 4 has described a method for synthesizing urea with a small volume of necessary equipment per unit production amount, wherein the condensation of a gas mixture of unreacted ammonia and carbon dioxide and the synthesis of urea are performed in a single vessel.

In the disclosure, this method for synthesizing urea includes: feeding a gas mixture obtained by stripping unreacted ammonia and unreacted carbon dioxide with use of raw material carbon dioxide and an absorbing medium to the bottom of a vertical condensation synthesizing tower; feeding raw material liquid ammonia to the bottom and middle of the vertical condensation synthesizing tower; condensing the gas mixture by cooling the part ranging from the bottom to the middle of the vertical condensation synthesizing tower while carrying out the synthesis of urea; introducing the generated urea synthesis solution into the top of a stripper from the top of the vertical condensation synthesizing tower; and subjecting unreacted ammonia and carbon dioxide in the urea synthesis solution to stripping with use of raw material carbon dioxide.

Patent Document 5 has disclosed that the height of an apparatus for a synthesis step can be reduced drastically in a $CO_2$ stripping urea process by placing a synthesis reactor horizontally.

Patent Documents 6 and 7 have disclosed a process wherein a urea synthesis solution coming out of a horizontal submerged condenser is introduced into a synthesis reactor with use of an ejector.

Patent Document 1: International Publication WO 00/43358
Patent Document 2: International Publication WO 01/72700
Patent Document 3: Japanese Patent Laid-Open No. 10-182587
Patent Document 4: Japanese Patent Laid-Open No. 2002-20360
Patent Document 5: Japanese Patent Laid-Open No. 59-122452
Patent Document 6: Japanese Patent Laid-Open No. 11-180942
Patent Document 7: International Publication WO 00/00466

DISCLOSURE OF THE INVENTION

Problems to be Solved by the Invention

A conventional vertical submerged condenser for condensing a gas from a stripper has been provided above a synthesis reactor for synthesizing urea in the vertical direction.

However, the vertical submerged condenser has cooling pipes and further a tubesheet fixing the cooling pipes thereon and is therefore heavy. The installation of the condenser above the synthesis reactor means the installation of the condenser at a relatively high position. When such a heavy article is installed at a high position, the equipment installation and fixation thereof are not easy, and cost thereof tends to rise.

In FIG. 2 of Patent Document 1, a vertical combi-reactor having a condensation zone is placed at a position lower than that of a reactor in the sheet of the drawing. However, in the vertical combi-reactor shown therein, a process fluid is made to flow on the tube side. Therefore, the residence time thereof is short. Thus, since the generation of water by urea synthesis is substantially absent within the tube, resulting in no absorption effect of ammonia and carbon dioxide gases, the vapor pressure-reducing effect attributed to the generation of urea, of which vapor pressure is zero, cannot be expected. Moreover, the vertical combi-reactor also presents problems such as the difficulty in evenly dispersing the process fluid to each tube and an increase in weight and in cost due to two thick tubesheets necessary for enduring a high pressure exceeding 13 MPa.

Patent Document 4 shows a vertical condensation synthesizing tower having a condensation section in a lower part and a synthesis section in an upper part. However, the condensation section and the synthesis section shown therein are not divided from each other and are in a region in a single vessel. Thus, this equipment must be placed at a high position or installed with a pump or a blower for supplying a synthesis solution from this region to a stripper.

An object of the present invention is to provide an apparatus for synthesizing urea, which is capable of installing a heavy condenser at a relatively low position and can circumvent problems associated with letting a process fluid flow within a tube in the condenser.

Another object of the present invention is to provide a revamping method, which can revamp an existing apparatus for synthesizing urea to thereby obtain the apparatus for synthesizing urea as described above.

Means for Solving the Problems

The present invention is as described below.

1) An apparatus for synthesizing urea comprising:
a synthesis reactor for reacting ammonia with carbon dioxide to obtain a urea synthesis solution containing urea, unreacted ammonia, unreacted carbon dioxide and water;
a stripper for stripping the urea synthesis solution with use of at least a part of raw material carbon dioxide to separate a gas mixture containing the unreacted ammonia and the unreacted carbon dioxide;
a vertical submerged condenser having a shell and tube structure for condensing the gas mixture in an absorbing medium on the shell side while cooling the gas mixture with a cooling medium passing through the tube side; and
recycling means for recycling a liquid obtained from the vertical submerged condenser to the synthesis reactor,
wherein the vertical submerged condenser is placed below the synthesis reactor.

2) The apparatus according to 1), wherein the recycling means comprises an ejector of which driving source is raw material ammonia.

3) The apparatus according to 1) or 2), wherein the synthesis reactor and the vertical submerged condenser are divided from each other and integrated with each other, and the synthesis reactor is placed above the vertical submerged condenser.

4) The apparatus according to 3), further comprising a scrubber for scrubbing a gas that has not been condensed in the vertical submerged condenser, wherein the scrubber is placed in the interior of the vertical submerged condenser.

5) The apparatus according to 1) or 2), further comprising a scrubber for scrubbing a gas that has not been condensed in the vertical submerged condenser, wherein the vertical submerged condenser and the scrubber are integrated with each other.

6) The apparatus according to 5), wherein the scrubber is placed in the interior of the vertical submerged condenser.

7) The apparatus according to 5) or 6), wherein the synthesis reactor is a horizontal type.

8) A method for revamping an existing apparatus for synthesizing urea having a synthesis reactor for reacting ammonia with carbon dioxide to obtain a urea synthesis solution containing urea, unreacted ammonia, unreacted carbon dioxide and water, comprising installing the apparatus with:
a stripper for stripping the urea synthesis solution with use of at least a part of raw material carbon dioxide to separate a gas mixture containing the unreacted ammonia and the unreacted carbon dioxide;
a vertical submerged condenser having a shell and tube structure for condensing the gas mixture in an absorbing medium on the shell side while cooling the gas mixture with a cooling medium passing through the tube side; and
recycling means for recycling a liquid obtained from the vertical submerged condenser to the synthesis reactor,
wherein the vertical submerged condenser is placed below the synthesis reactor.

9) A method for revamping an existing apparatus for synthesizing urea having:
a synthesis reactor for reacting ammonia with carbon dioxide to obtain a urea synthesis solution containing urea, unreacted ammonia, unreacted carbon dioxide and water;
a stripper for stripping the urea synthesis solution with use of at least a part of raw material carbon dioxide to separate a gas mixture containing the unreacted ammonia and the unreacted carbon dioxide; and
a vertical falling liquid film condenser for condensing the gas mixture, comprising installing the apparatus with:
a vertical submerged condenser having a shell and tube structure for condensing the gas mixture in an absorbing medium on the shell side while cooling the gas mixture with a cooling medium passing through the tube side; and
recycling means for recycling a liquid obtained from the vertical submerged condenser to the synthesis reactor,
wherein the vertical submerged condenser is placed below the synthesis reactor.

10) The revamping method according to 9), wherein the vertical falling liquid film condenser includes cooling means, and
the method further comprises providing the apparatus with a line for directing a liquid at the outlet of the stripper to the cooling means.

Advantages of the Invention

According to the present invention, an apparatus for synthesizing urea is provided, which is capable of installing a heavy condenser at a relatively low position and can circumvent problems associated with letting a process fluid flow within a tube in the condenser.

A revamping method is also provided, which can revamp an existing apparatus for synthesizing urea to thereby obtain the apparatus for synthesizing urea as described above.

DESCRIPTION OF SYMBOLS

Figure 1:
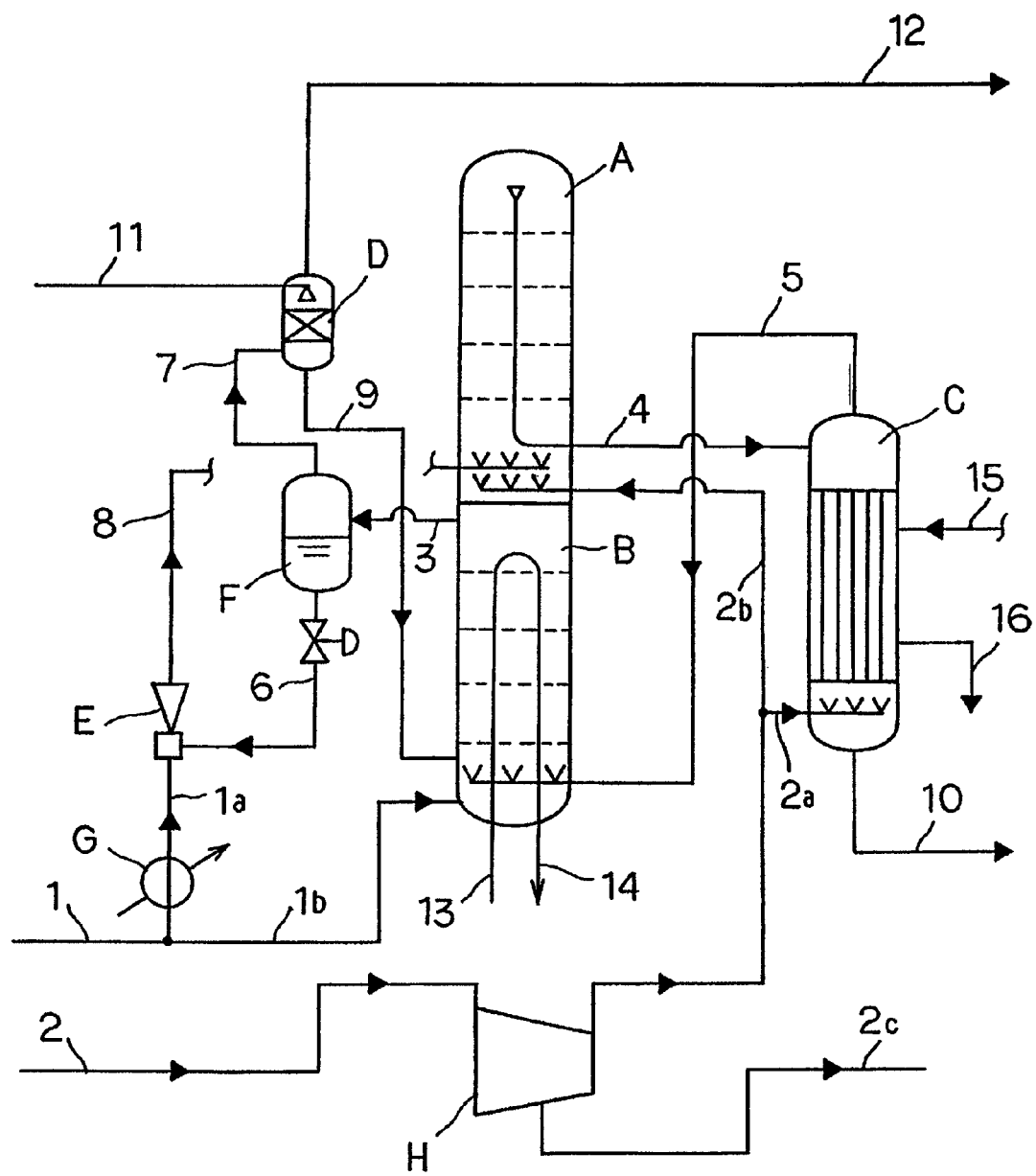
FIG. 1 is a flow diagram showing one embodiment of an apparatus for synthesizing urea of the present invention.

A: synthesizing tower
B: condenser
C: stripper
D: scrubber
E: ejector
F: gas-liquid separator
G: ammonia preheater
H: carbon dioxide compressor
I: vertical falling liquid film condenser
1: raw material ammonia
2: raw material carbon dioxide
3: synthesis solution at condenser outlet
4: synthesis solution at synthesis reactor outlet
5: outlet gas at stripper top
6: outlet liquid at gas-liquid separator
7: outlet gas at gas-liquid separator
8: liquid at ejector outlet
9: liquid at scrubber outlet
10: liquid at stripper outlet
11: recycled carbamate liquid
12: gas at scrubber outlet
13: cooling medium at tube inlet of condenser (boiler water)
14: cooling medium at tube outlet of condenser (boiler water and steam)
15: steam for heating stripper shell
16: condensed water at outlet of stripper shell
21: gas containing ammonia and carbon dioxide obtained from decomposition apparatus
22: urea solution obtained from the decomposition apparatus
23: molten urea
24: granular urea

BEST MODE FOR CARRYING OUT THE INVENTION

Hereinafter, the present invention will be described with reference to drawings. However, the present invention is not intended to be limited to them. The positional relationships of component parts of an apparatus in the vertical direction are shown in FIGS. 1 to 5.

Hereinafter, a vertical submerged condenser is simply referred to as a condenser in some cases.

The vertical submerged condenser is a condenser having a vertical shell and tube heat exchanger structure wherein a cooling pipe is completely immersed in a liquid phase on the shell side.

FIG. 1 is a flow diagram showing one embodiment of an apparatus for synthesizing urea of the present invention, which is suitable for a $CO_2$ stripping urea producing process. This apparatus includes a synthesis reactor A including a synthesis zone, a condenser B including a condensation zone, a stripper C for treating unreacted components in a synthesis solution 4 at the outlet of the synthesis reactor, a scrubber D for absorbing uncondensed gases from the condenser into an absorbing medium, and an ejector E for pressurizing.

In this contest, the synthesis zone means a region wherein of the reactions of the formulas 1 and 2 described later, mainly the reaction of the formula 2 progresses, and the condensation zone means a region for condensing an ammonia gas and/or a carbon dioxide gas into the absorbing medium, wherein the reaction of the formula 1 as well as the reaction of the formula 2, which is the dehydration reaction of ammonium carbamate formed by the reaction of the formula 1, progresses.

These component parts may be installed separately or may be installed, if desired, in combination such as the synthesis reactor and the condenser or the condenser and the scrubber. Moreover, the synthesis reactor may be a vertical or horizontal type, which is appropriately determined from the viewpoint of cost efficiency and so on.

In the present invention, the condenser is placed below the synthesis reactor. Specifically, the upper end of the condenser is provided lower than the upper end of the synthesis reactor in the vertical direction.

In the condensation zone and the synthesis zone, ammonium carbamate (hereinafter, referred to as carbamate in some cases) is formed by the reaction of ammonia and carbon dioxide, and the formed carbamate is dehydrated to thereby form urea, as shown in the formulas 1 and 2 described below. The reaction rate of carbamate formation is high, and the urea formation reaction by the dehydration of carbamate is an equilibrium reaction.

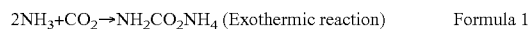
$2NH_3 + CO_2 \rightarrow NH_2CO_2NH_4$ (Exothermic reaction)   Formula 1

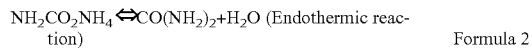
$NH_2CO_2NH_4 \Leftrightarrow CO(NH_2)_2 + H_2O$ (Endothermic reaction)   Formula 2

Raw material liquid ammonia 1 is pressurized to a desired pressure by an ammonia pump (not shown), and a part 1a thereof is heated by a heat exchanger G and supplied to the ejector E. A urea synthesis solution 6 from the condenser B is supplied to the ejector and pressurized. On the other hand, raw material gaseous carbon dioxide 2 is pressurized to a desired pressure by a carbon dioxide compressor H, and the greater part 2a thereof is supplied to the stripper C. The remaining portion 2b of the carbon dioxide is supplied to the synthesis reactor A for the purpose of controlling the temperature of the synthesis reactor and supplying oxygen for corrosion prevention. Air for corrosion prevention (not shown) is usually supplied to the first stage suction side or to the middle stage of the carbon dioxide compressor. The heat exchanger G can appropriately adopt a heat exchanger known in the art having a structure that can heat raw material ammonia. A fluid having a desired temperature level can be used appropriately as a heat medium for heating in the heat exchanger G.

A small portion of the whole ammonia raw material may be supplied, to the condenser, as raw material ammonia 1b for the corrosion prevention of welds of a condenser tubesheet. The feed line for this raw material ammonia 1b is not always necessary.

Although carbon dioxide 2c is used as a stripping agent in a downstream decomposition step, the line for this carbon dioxide 2c is not always necessary.

An ammonia-containing synthesis solution 8 from the ejector E is supplied to the synthesis reactor, as with carbon dioxide.

This ejector constitutes recycling means for recycling the liquid 6 obtained from the condenser B to the synthesis reactor A. In FIG. 1, the recycling means includes a gas-liquid separator F, the ejector E, and the lines 3, 6, and 8. The line 6 is provided with a regulating valve for the liquid level regulation of the gas-liquid separator F. Although alternative pressurizing means such as a pump may be used instead of the ejector for recycling, the ejector is preferable because of its simple structure and excellent endurance and maintainability. An operating condition (pressure difference between the lines 6 and 8) for the ejector may be set to, for example, not less than 0.2 Mpa and not more than 1 MPa.

In the synthesis zone in the interior of the synthesis reactor, the urea synthesizing reaction proceeds, preferably close to an equilibrium synthesis rate, to thereby synthesize urea. In the interior of the synthesis reactor, it is preferred that urea is synthesized at a pressure of not less than 13 MPaG and not more than 25 MPaG (G in the pressure unit denotes a gage pressure), at a temperature of not less than 170° C. and not more than 210° C., at a mole ratio of ammonia (including ammonia that has been converted to ammonium carbamate and urea) to carbon dioxide (including carbon dioxide that has been converted to ammonium carbamate and urea) (hereinafter, referred to as N/C) of not less than 3.0 and not more than 4.5, at a mole ratio of water (excluding water formed by the urea synthesizing reaction) to carbon dioxide (including carbon dioxide that has been converted to ammonium carbamate and urea) (hereinafter, referred to as H/C) of not more than 1.0, and with a residence time of not less than 10 minutes and not more than 40 minutes.

The synthesis temperature can be controlled, for example, by the preheating temperature of the ammonia 1a driving the ejector and/or by the amount of the carbon dioxide 2b supplied to the synthesis reactor. N/C can be determined, for example, by continuously measuring the density of the liquid 4 at the outlet of the synthesis reactor with a density meter or by regularly sampling and quantitatively analyzing the liquid 4 at the outlet of the synthesis reactor. N/C can be adjusted, for example, by adjusting the amount of the ammonia 1a supplied to the ejector. H/C is often determined depending on the amount of water necessary for the absorption of unreacted substances (ammonia and carbon dioxide) in a recovery apparatus (not shown in FIG. 1) for recovering the unreacted substances discharged from the synthesis reactor. Since water inhibits the urea synthesizing reaction in terms of equilibrium (lower H/C is better in terms of synthesis equilibrium), it is preferred that the amount of water supplied to this recovery apparatus is a requisite minimum. The recovery apparatus will be described later.

In the synthesis reactor, the urea synthesis rate with respect to carbon dioxide is determined depending on chemical equilibrium and is on the order of not less than 60% and not more than 75% when the N/C range is not less than 3.0 and not more than 4.5.

The synthesis rate with respect to carbon dioxide is the ratio of the number of moles of the carbon dioxide that has been converted to urea among the supplied carbon dioxide to the number of moles of the carbon dioxide supplied to the equipment or the region to be considered, and is usually indicated in %.

The synthesis pressure set to 13 MPaG or more is preferable from the viewpoint of allowing for the adoption of an operating pressure having a margin for the synthesis equilibrium pressure at a temperature (170° C. or higher) preferable for urea synthesis and from the viewpoint of preventing a decrease in the synthesis rate attributed to vaporization. The synthesis pressure set to 25 MPaG or less is preferable from the viewpoint of allowing for reduction in energy for pressurizing the raw material ammonia, the raw material carbon dioxide, and the unreacted carbamate liquid 6 and from the viewpoint of equipment cost.

The carbamate liquid refers to a liquid obtained by recovering the unreacted ammonia and carbon dioxide as an aqueous solution of ammonium carbamate in the recovery step downstream from the synthesis step.

The synthesis temperature set to 170° C. or higher is preferable from the viewpoint of preventing a decrease in the reaction rate of urea formation. Moreover, the synthesis temperature set to 210° C. or lower is preferable from the viewpoint of preventing a rise in the risk of so-called active corrosion in addition to an increase in a corrosion rate.

N/C is preferably 3.0 or more from the viewpoint of the equilibrium synthesis rate and is preferably 4.5 or less from the viewpoint of preventing a gaseous phase from being easily generated due to an increased ammonia vapor pressure.

The stoichiometric ratio of ammonia to carbon dioxide (N/C) in urea synthesis is 2 as shown in the formulas 1 and 2 described above. Actually, the state where excessive unreacted ammonia is present as a result of excessive ammonia supply is preferable for increasing the urea equilibrium synthesis rate.

H/C is preferably 1.0 or less, more preferably 0.7 or less, from the viewpoint of the urea synthesis rate. H/C may be zero. Actually, water often exist to a certain extent because H/C is often determined depending on the amount of water necessary for the absorption of unreacted substances (ammonia and carbon dioxide) in a recovery apparatus (not shown in FIG. 1) for recovering the unreacted substances coming out of the apparatus for synthesizing urea. H/C may be set to, for example, 0.4 or more.

The residence time of the process fluid in the synthesis reactor set to 10 minutes or more is preferable from the viewpoint of causing the progress of the urea synthesizing reaction. The residence time is preferably 40 minutes or less because, even if the residence time exceeds 40 minutes, the synthesis rate has already reached nearly the equilibrium synthesis rate and cannot be practically expected to further rise.

Urea is synthesized in the condensation zone within the condenser B and in the synthesis zone within the synthesis reactor A. A urea-containing effluent substance 4 coming out of the synthesis reactor is supplied to the stripper C. The effluent substance 4 at the outlet of the synthesis reactor contains the synthesized urea, water, carbamate, and unreacted ammonia as liquid phases and a portion of unreacted ammonia and carbon dioxide as gaseous phases together with inert gases.

In this context, the inert gases are a general term for air introduced for preventing the corrosion of the apparatus for synthesizing urea composed of, for example, the synthesis reactor, the stripper, the condenser, the scrubber, and the piping connecting them and so on, and for impurities such as hydrogen and nitrogen contained in the raw material carbon dioxide.

The effluent substance 4 from the synthesis reactor, after being supplied to the stripper C, is heated by steam for heating, and the carbamate contained in the effluent substance from the synthesis reactor is thereby thermally decomposed. Moreover, the unreacted ammonia and the unreacted carbon dioxide in the effluent substance from the synthesis reactor are $CO_2$-stripped by the supplied raw material carbon dioxide 2a and divided into gaseous components 5 containing carbon dioxide, ammonia and inert gases and into a synthesis solution 10. This synthesis solution usually has a urea concentration of not less than 40% by mass and not more than 60% by mass inclusive.

The stripping refers to an operation wherein a component dissolved in a solution is released from the liquid by heating and/or by contact with a stripping agent (usually, a gas that is insoluble or poorly soluble in the solution) and separated as a gaseous phase.

The stripper C has a shell and tube heat exchange structure, wherein on the shell side, the steam 15 for heating is supplied, and condensed water 16, a condensate of this steam, is discharged. The effluent substance from the synthesis reactor is heated when passing through the tube side. As described above, the stripping performed both by heating and by carbon dioxide is preferable because not only excellent stripping effect but also carbamate-decomposing effect is obtained. Since the stripper C also has the function of gas-liquid separation, it is not necessary to additionally provide a gas-liquid separator for separating the effluent substance 4 from synthesis reactor into gas and liquid.

The gaseous components 5 from the stripper are supplied to the condenser. For this purpose, the stripper is connected to the shell side of the condenser. On the other hand, the synthesis solution 10 from the stripper is sent to a decomposition apparatus (not shown in FIG. 1), in which the urea component thereof is further purified.

An absorbing medium is supplied to the scrubber D. Recycled carbamate liquid 11 recovered in the decomposition apparatus and in the recovery apparatus (not shown in FIG. 1) is used as this absorbing medium. The decomposition apparatus, the recovery apparatus, and the recycled carbamate liquid will be described later.

Here, the recycled carbamate liquid 11 is supplied as the absorbing medium to the scrubber D and supplied from the line 9 to the condenser after absorbing a portion of ammonia and carbon dioxide gas contained in the gaseous components 7 by contact with the gaseous components 7 from the condenser B. Ammonia, carbon dioxide gas, and inert gases that have not been absorbed into the recycled carbamate liquid 11 are sent from the line 12 to the recovery apparatus.

The scrubbing refers to an operation wherein a certain component in gas is absorbed into liquid by contact between the gas and the liquid to thereby clean the gas.

It is preferred that the condenser is operated at a pressure of not less than 13 MPaG and not more than 25 MPaG, at a temperature of not less than 160° C. and not more than 200° C., at N/C of not less than 2.5 and not more than 4.0, at H/C of not more than 1.0, and with a residence time of not less than 10 minutes and not more than 30 minutes.

The N/C of the condenser is secondarily determined depending on the N/C of the synthesis reactor. Specifically, the composition of the gas 5 at the outlet of the stripper is determined mainly depending on the N/C of the synthesis reactor, with the result that the N/C of the condenser was also determined. The H/C of the condenser is determined depending on the amount of water necessary for the absorption of unreacted substances (ammonia and carbon dioxide) in a recovery apparatus for recovering the unreacted substances coming out of the apparatus for synthesizing urea. Since water inhibits the urea synthesizing reaction in terms of equilibrium (lower H/C is better in terms of synthesis equilibrium), it is preferred that the amount of water supplied to this recovery apparatus is a requisite minimum.

The condensation section and the stripper are operated at substantially the same pressure as that for the synthesis reactor.

The temperature of the process fluid within the condenser is preferably 160° C. or higher from the viewpoint of the reaction rate of urea formation and is preferably 200° C. or lower from the viewpoint of suppressing both a decrease in the condensation rate with an increase in the vapor pressure and the corrosion of the equipment materials.

The N/C of the process fluid within the condenser is preferably 2.5 or more from the viewpoint of suppressing a decrease in the condensation rate attributed to an increase in the partial pressure of carbon dioxide in the urea synthesis solution and is preferably 4.0 or less from the viewpoint of suppressing a decrease in the condensation rate resulting from an increase in the vapor pressure of ammonia.

H/C is preferably 1.0 or less from the viewpoint of the urea synthesis rate.

The residence time within the condenser is preferably 10 minutes or more from the viewpoint of suppressing both an increase in the vapor pressure attributed to a decrease in the urea synthesis rate and a decrease in the condensation rate. The residence time is preferably 30 minutes or less because, even if the residence time exceeds 30 minutes, the urea synthesis rate cannot be expected to remarkably rise.

The carbamate liquid 9, which has absorbed a portion of the gaseous components 7 supplied from the stripper C through the condenser B and the gas-liquid separator F to the scrubber D, is supplied to the condenser. In the condenser, the carbamate liquid 9 and gaseous components 5 contact with each other, and ammonia and carbon dioxide are absorbed into the carbamate liquid and condensed, followed by the carbamate forming reaction represented by the formula 1 and the carbamate dehydration reaction represented by the formula 2 to thereby form urea.

The conversion ratio with respect to carbon dioxide in the condenser is, for example, not less than 20% and not more than 60%.

Ammonia and carbon dioxide that have not been condensed in the condensation zone are separated together with inert gases in the top section of the condenser or in the gas-liquid separator and sent to the recovery apparatus or to the scrubber. Here, a gas mixture of them is separated from the liquid in the gas-liquid separator F and sent to the scrubber D.

The liquid 6 obtained from the gas-liquid separation of the fluid 3 at the outlet of the condenser is supplied to the ejector E, then sent to the synthesis reactor where raw material ammonia is used as a driving source, and subjected to the further urea synthesizing reaction.

Hereinafter, each component part of the apparatus will be described in detail.

The synthesis reactor A may be a vertical- or horizontal-type reactor, the interior of which is installed with baffle plates, a gas distributor, and so on. Moreover, the synthesis reactor may adopt, if desired, a structure wherein the synthesis reactor is constructed integrally with the condenser and so on. However, the synthesis reactor and the condenser, even when constructed integrally, are divided from each other by a partition plate or the like and constructed independently.

The stripper can appropriately adopt a structure that is capable of performing gas-liquid contact and/or a structure that can achieve the decomposition of carbamate in the synthesis solution 4 and the emission of dissolved gases by heating.

The stripper may have a vertical shell and tube heat exchange structure, for example, as shown in FIG. 1. In this case, a heat medium such as steam and the synthesis solution 4 are supplied to the shell side and to the tube side, respectively, and heat may be supplied from the shell side to the tube side. Other than such a structure, a plate tower and a packed tower may also be used as the stripper. A combination thereof may also be adopted.

The structure of the scrubber can appropriately adopt a structure that is capable of scrubbing and may adopt a packed tower packed with packing, a shell and tube structure, a plate tower, and a combination thereof. The scrubber is operated at substantially the same pressure as that for the synthesis reactor and usually at a temperature of not less than 100° C. and not more than 180° C. In the scrubber, absorption heat is generated by the absorption of gases. The scrubber having the shell and tube structure allows for the removal and recovery of the absorption heat by a cooling medium.

The scrubber may be built in the condenser or may be constructed integrally with the condenser, as appropriate.

The condenser can adopt, as appropriate, a vertical submerged condenser having a structure that can condense the gaseous components, absorb ammonia and carbon dioxide, and bring about the urea synthesizing reaction represented by the reaction formulas 1 and 2. The vertical type has an advantage in easily distributing gas evenly within the condenser and easily securing a small installation area and a long residence time of gas. Since the urea synthesizing reaction occurs in a liquid phase, it is desirable to insert a cooling pipe into the liquid. Therefore, a vertical submerged condenser is used.

The condenser may adopt, for example, as shown in FIG. 1, a structure wherein a U tube is installed as cooling means. This structure is suitable for the submerged condenser. That is, the U tube is easily brought into the state where it is completely immersed in the liquid phase. A cooling medium such as boiler water may be supplied to the tube side. Alternatively, a process fluid such as liquid ammonia and a urea liquid may be allowed to flow as a cooling medium to thereby perform the cooling of the fluid on the shell side simultaneously with the preheating or heating of the process.

If the U tube is used, only one tubesheet suffices. This structure is effective for weight saving.

Moreover, the condenser and the synthesis reactor may be constructed integrally, if desired.

An example of the condenser constructed integrally with the vertical synthesis reactor is shown in FIG. 1. The condenser is installed below the synthesis reactor so that the condenser is integrated with the lower part of the synthesis reactor via a partition plate.

The pressurized raw material ammonia 1a and the liquid 6 obtained from the condenser are supplied to the ejector E, and the mixed fluid 8 of them is supplied to the lower part of the synthesis reactor A. A portion 2b of the pressurized raw material carbon dioxide containing air (supplied from, e.g., the intermediate stage of the pressurizing means H) is supplied to the synthesis reactor. These supplied raw materials ascend in the synthesis reactor, during which reactions according to the reaction formulas 1 and 2 occur in the synthesis reactor to thereby form urea and so on. It is preferred that baffle plates for promoting mixing and reactions are installed within the synthesis reactor. The synthesis solution in which the reactions have preferably reached nearly equilibrium passes through downward the down pipe having an inlet installed in the upper part of the synthesis reactor and is supplied from the line 4 to the upper part of the stripper. The pressurized raw material carbon dioxide 2a is supplied from the lower part of the stripper and strips unreacted ammonia in the synthesis solution 4 and decomposition products of carbamate.

The stripper shown in FIG. 1 has a vertical shell and tube heat exchange structure. On the tube side, the unreacted substance (carbamate) in the synthesis solution 4 and excessive ammonia are stripped as gaseous components (ammonia and carbon dioxide) by countercurrent contact between the synthesis solution 4 from the synthesis reactor and the raw material carbon dioxide 2a. Steam is supplied to the shell side and used as a heat source for the decomposition of carbamate.

The gaseous components 5 from the upper part of the stripper are supplied to the lower part of the condenser. The carbamate liquid 9 from the scrubber is also supplied to the lower part of the condenser.

A U tube is installed as cooling means within the condenser. Water (boiler water) 13 for cooling is supplied to the U tube, and a fluid 14 (mixed fluid of boiler water and steam), which has been subjected to the cooling, is discharged from the U tube.

The carbamate liquid 9 supplied as an absorbing medium to the shell portion of the condenser and the gaseous components 5 from the stripper are brought into contact with each other and cooled while ascending in the interior of the condenser. The gaseous components are condensed and absorbed into the carbamate liquid to thereby form carbamate, followed by the further urea synthesizing reaction.

In FIG. 1, the gas-liquid separator F is installed independently. In the gas-liquid separator, the fluid 3 discharged from the condenser is divided into gaseous components 7 and a liquid 6. The gases and the liquid are supplied to the scrubber and to the ejector, respectively.

As described above, the condenser is placed below the synthesis reactor, whereby a cooling pipe such as a U tube and a tubesheet thereof having huge weights can be placed at a relatively low position, thereby facilitating equipment installation and fixation.

The condenser provided with the U tube in the upper part has a structure wherein the U tube extends downward from the tubesheet. In such a case, when a gaseous phase portion is developed in the interior of the condenser, the gas-liquid interface comes into contact with the outer surface of the tube. That is, the tube spans both the gaseous phase portion and the liquid phase portion. In such a situation, the tube might be caused to be susceptible to corrosion attributed to the condensation of carbamate. However, in the condenser shown in FIG. 1, the tubesheet is provided in the lower part, particularly the bottom, of the condenser, and the U tube extends upward from the tubesheet. Moreover, a zone free of the U tube can be provided in the upper part of the condenser. Thus, the U tube can be immersed completely in the liquid even if the gaseous phase portion exists in the interior of the condenser. This structure is preferable because of posing no risk of the corrosion as described above.

In the condenser constructed integrally with the synthesis reactor, the U tube has no other choice but to extend downward from the tubesheet if the condenser is provided above the synthesis reactor. However, even when the condenser is constructed integrally with the synthesis reactor, a zone free of the U tube can be provided in the upper part of the condenser as described above by placing the condenser below the synthesis reactor. This structure is preferable because the corrosion as described above can be prevented.

The urea synthesis solution obtained in the synthesis reactor may be subjected to gas-liquid separation in the top section of the synthesis reactor or may be supplied directly as a gas-liquid mixed phase to the stripper without providing gas-liquid separation means within the synthesis reactor.

Figure 6:
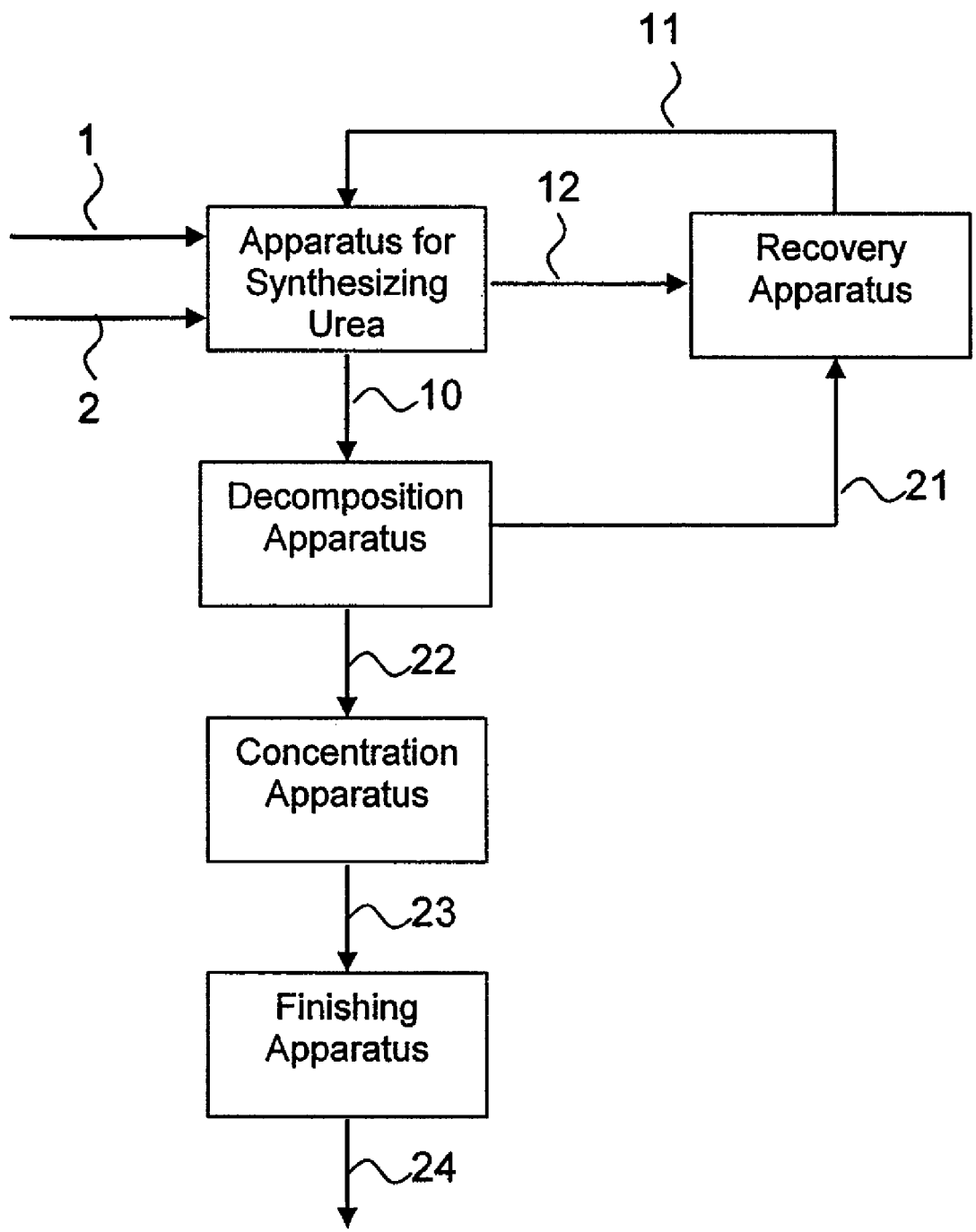
FIG. 6 is a flow diagram for illustrating a urea production plant.

An example of a urea production plant having an apparatus for synthesizing urea will be described. An outline of the urea production plant is shown in FIG. 6. The urea production plant includes an apparatus for synthesizing urea, a recovery apparatus, a decomposition apparatus, a concentration apparatus, and a finishing apparatus. Raw material ammonia 1 and raw material carbon dioxide 2 are supplied to the apparatus for synthesizing urea. A urea synthesis solution 10, which has undergone stripping, is sent from the apparatus for synthesizing urea to the decomposition apparatus.

In the decomposition apparatus, unreacted ammonia and carbamate contained in the urea synthesis solution are decomposed by heating the supplied urea synthesis solution under reduced pressure and separated as a gas 21 containing ammonia and carbon dioxide. The remaining liquid phase is sent as an aqueous solution of urea 22, for example, on the order of 68% by mass, to the concentration apparatus downstream of the decomposition apparatus.

In the concentration apparatus, moisture is almost completely evaporated and separated by heating under vacuum the aqueous solution of urea 22 obtained in the decomposition apparatus, to thereby obtain molten urea 23, for example, on the order of 99.7% by mass. This molten urea is sent to the finishing apparatus downstream of the concentration apparatus, in which the molten urea is then subjected to cooling and solidification and finished as granular urea 24.

On the other hand, the gas 21 containing ammonia and carbon dioxide, which has been separated in the decomposition apparatus, and a gas 12 containing ammonia, carbon dioxide, and inert gases, which has not been absorbed into a recycled carbamate liquid in the scrubber, are absorbed into water in the recovery apparatus and recovered as an aqueous solution of ammonium carbamate. This aqueous solution is pressurized and then returned as a recycled carbamate liquid 11 to the apparatus for synthesizing urea.

Figure 2:
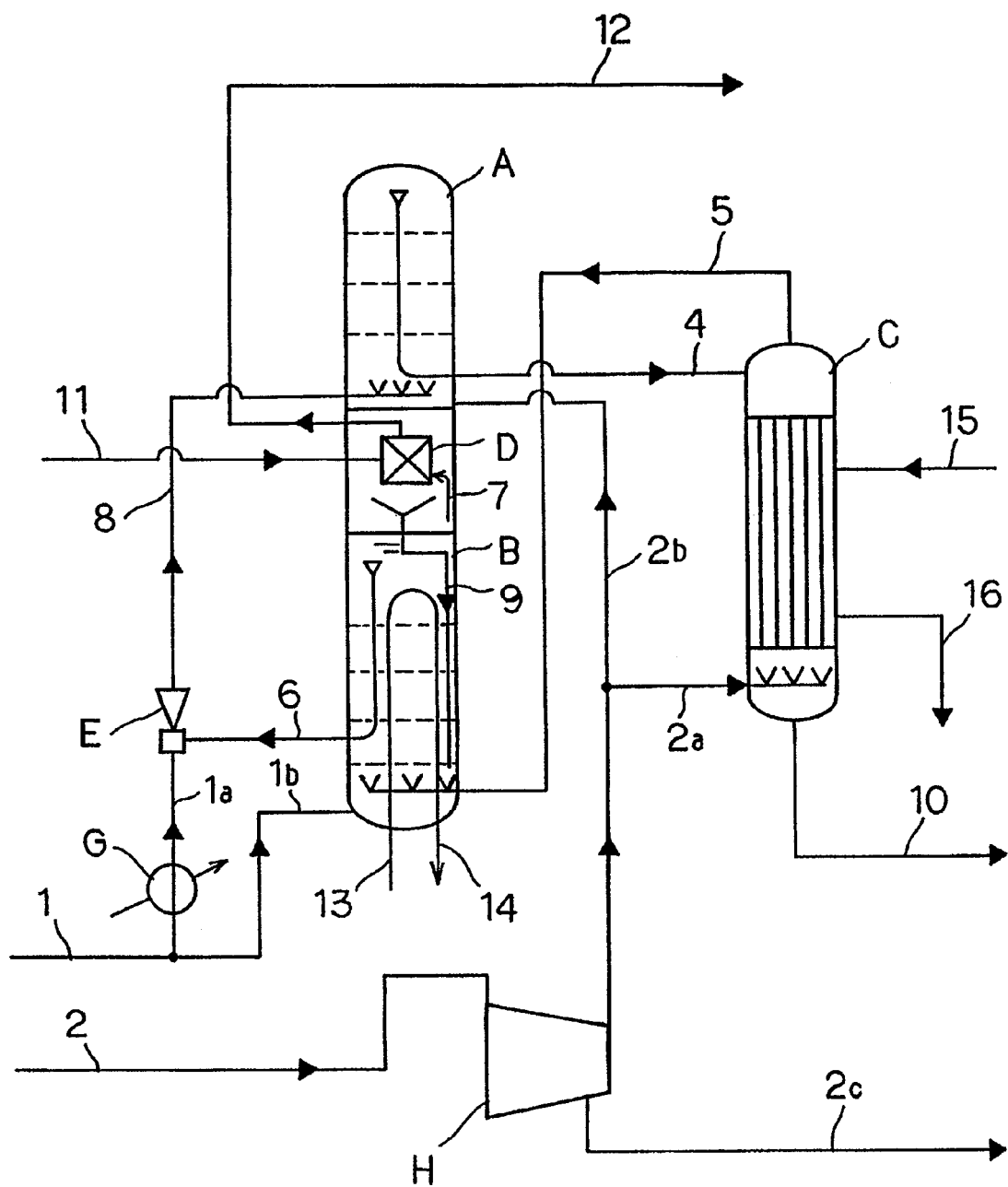
FIG. 2 is a flow diagram showing an alternative embodiment of the apparatus for synthesizing urea of the present invention.

An alternative embodiment of the present invention is shown in FIG. 2. This embodiment is different from the embodiment shown in FIG. 1 in that a scrubber D is installed between a synthesis reactor A and a condenser B. A gaseous phase portion exists in the upper part of the condenser, and the scrubber is provided within this gaseous phase portion.

A recycled carbamate liquid 11 is supplied to the installed scrubber D. In this embodiment, since the scrubber is installed within the synthesis reactor, it is unnecessary to additionally place not only a scrubber but also a gas-liquid separator. Thus, this structure is effective in terms of reduction in high-pressure piping, in equipment cost, and in construction cost. The gas-liquid separation can be performed by providing the gaseous phase portion in the upper part within the condenser B. Gaseous components 7 ascend from the gas-liquid interface and are then cleaned in the scrubber D and sent to a line 12, whereas liquid components 6 are sent to an ejector E through a down pipe having an inlet below the gas-liquid interface. A carbamate liquid 9, which has absorbed a portion of the gaseous components 7, is supplied through the down pipe to the lower part of the condenser.

Figure 3:
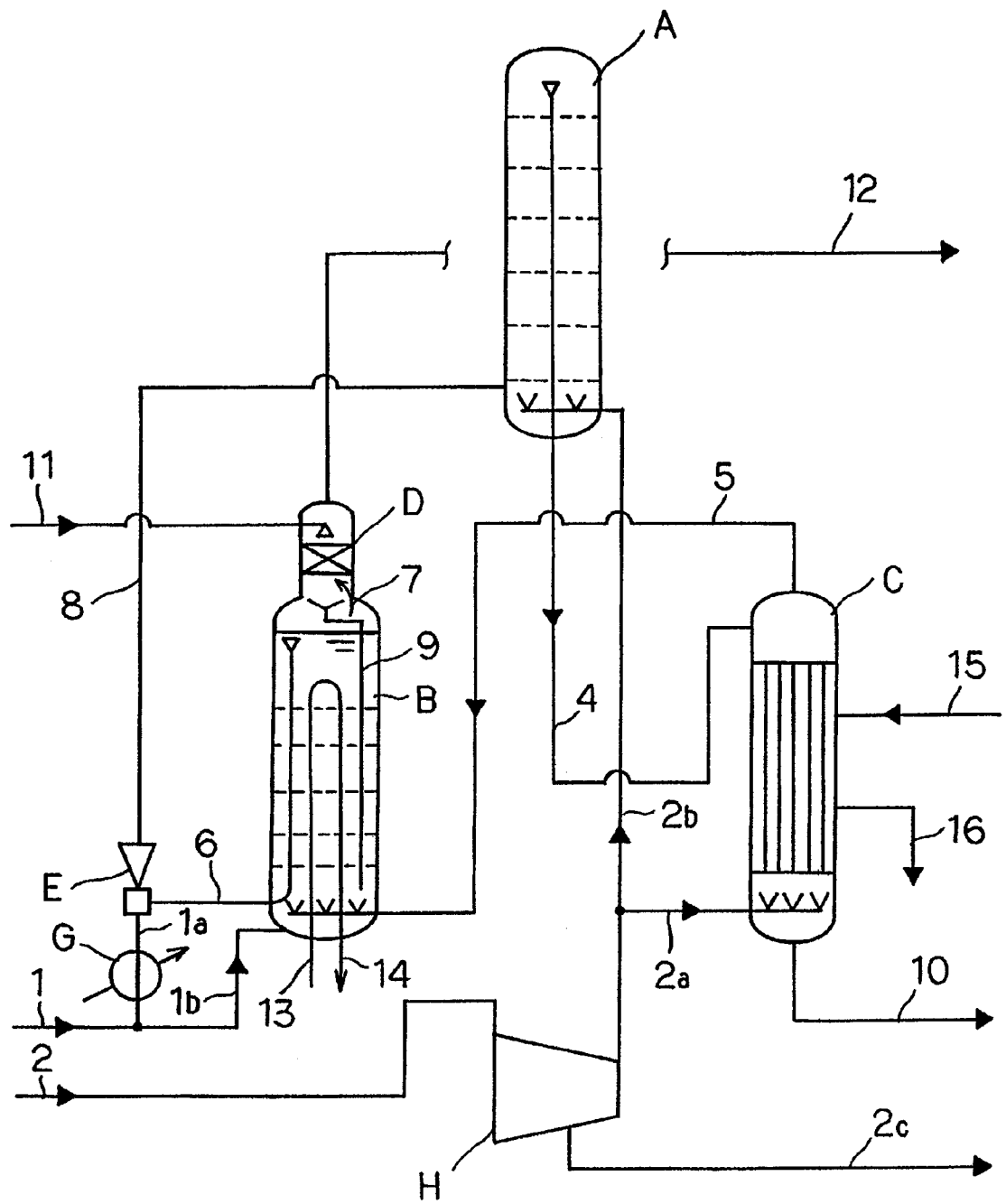
FIG. 3 is a flow diagram showing a further alternative embodiment of the apparatus for synthesizing urea of the present invention.

A further alternative embodiment of the present invention is shown in FIG. 3. In this embodiment, a scrubber D is built in a condenser B, and a synthesis reactor A is separately provided in isolation. As with the embodiment of FIG. 2, the scrubber is provided in a gaseous phase portion in the upper part of the condenser. Since gas-liquid separation is performed in the gaseous phase portion provided in the upper part of the condenser, no gas-liquid separator is required.

In this embodiment, the condenser and the synthesis reactor are constructed separately, thereby facilitating equipment manufacture and transport and works such as installation work. Moreover, this embodiment is suitable for revamping an apparatus for synthesizing urea in an old-type plant having an already-existing synthesis reactor, for example, a solution recycling (non-stripping) apparatus for synthesizing urea. By adding a stripper C, a condenser B, and recycling means for recycling a liquid obtained from the condenser to the synthesis reactor and so on to the plant having an already-existing synthesis reactor, wherein the condenser B is placed below the synthesis reactor A in the vertical direction to obtain this embodiment, it is possible to achieve enhancement in installed capacity and improvement in efficiency.

Figure 4:
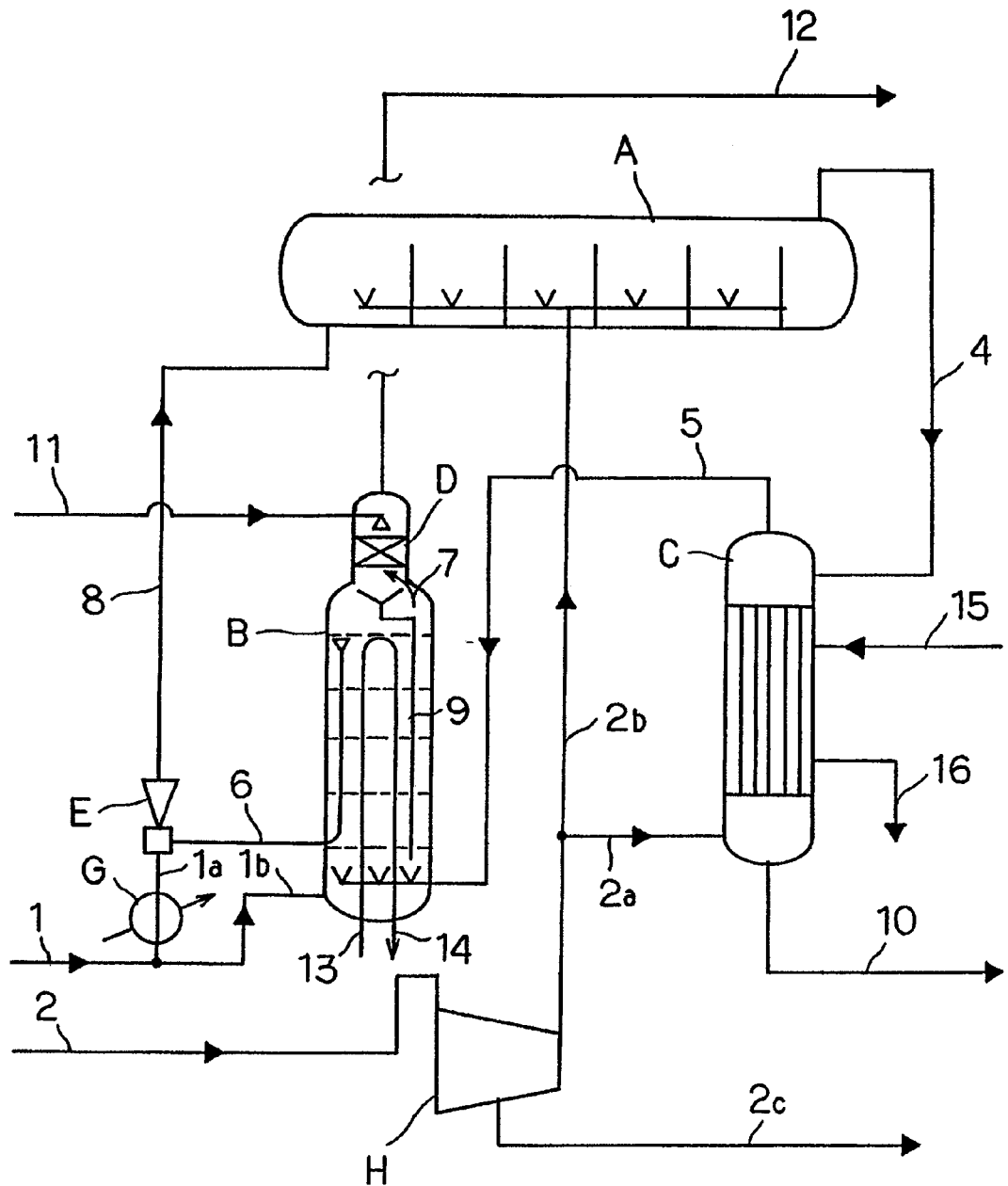
FIG. 4 is a flow diagram showing a further alternative embodiment of the apparatus for synthesizing urea of the present invention.

A further alternative embodiment of the present invention is shown in FIG. 4. This embodiment is modified from the embodiment shown in FIG. 103, by placing a synthesis reactor A horizontally. The use of the horizontally placed synthesis reactor can make the equipment height (particularly, at the top of the synthesis reactor) small and is effective for reduction in equipment cost.

Figure 5:
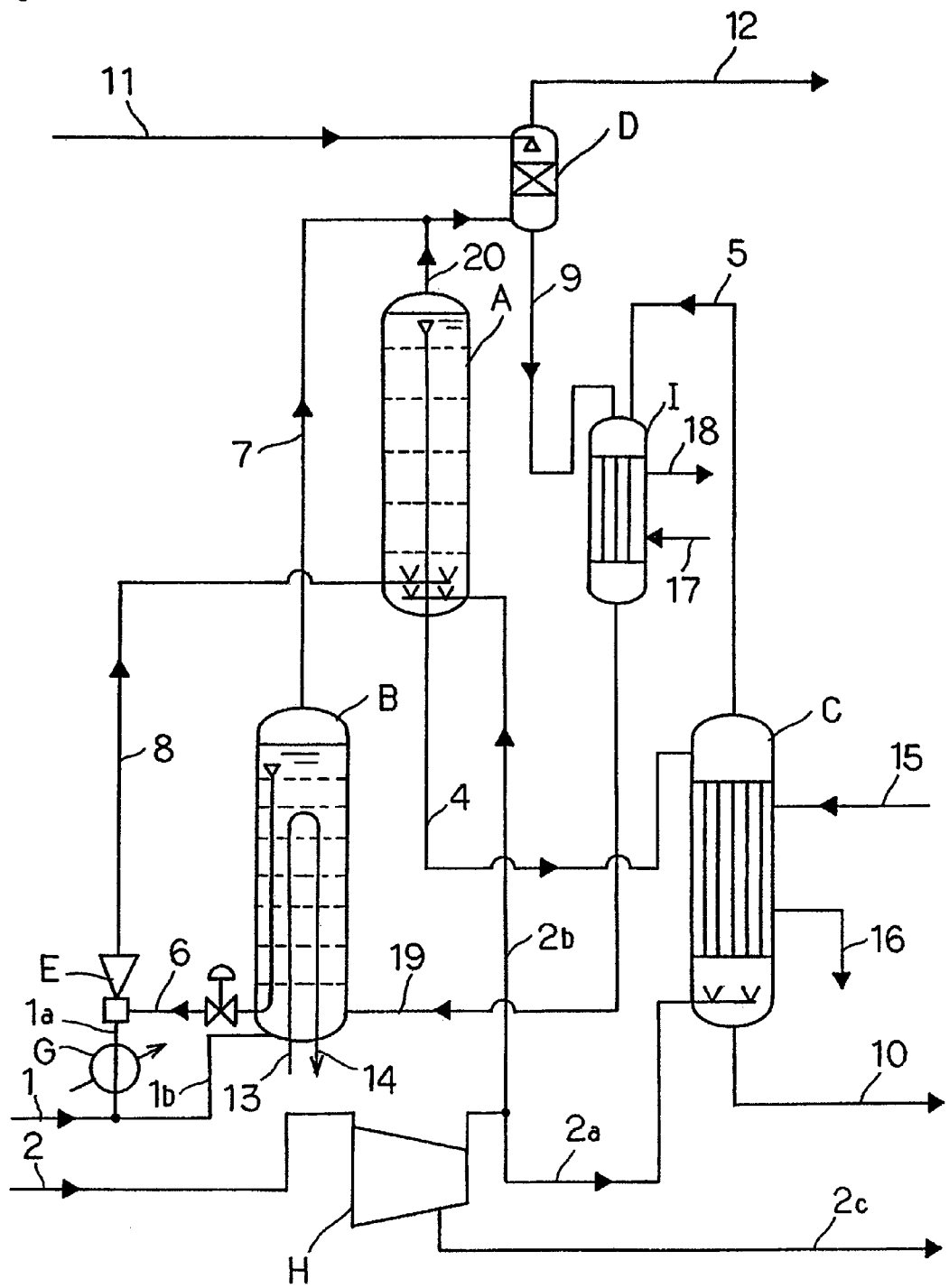
FIG. 5 is a flow diagram showing a further alternative embodiment of the apparatus for synthesizing urea of the present invention.

An existing stripping-type apparatus for synthesizing urea having a synthesis reactor, a stripper, and a vertical falling liquid film condenser may be revamped by installing this existing synthesizing apparatus with a vertical submerged condenser and recycling means for recycling a liquid obtained from the vertical submerged condenser to the synthesis reactor. An embodiment shown in, for example, FIG. 5 is suitable for boosting the production of urea by adding a vertical submerged condenser B and an ejector E as well as appropriate piping to an already-existing $CO_2$ stripping-type apparatus for synthesizing urea including a scrubber D additionally installed at a position higher than that of a synthesis reactor A and both a vertical falling liquid film condenser I and a synthesis reactor A installed at a position higher than that of a stripper C.

An effluent substance 19 (containing a gas mixture that has been separated in the stripper and has not been condensed in the condenser I) at the outlet of the vertical falling liquid film condenser I is supplied to the vertical submerged condenser B. For this purpose, the shell side of the vertical submerged, condenser is connected to the vertical falling liquid film condenser. A gas 20 at the outlet of the synthesis reactor is scrubbed in the scrubber D.

The vertical falling liquid film condenser I also includes cooling means for condensation. For example, boiler water 17 is supplied to the shell side of the condenser I and heated, and boiler water 18 partially converted to steam is discharged from the shell.

Alternatively, a liquid 10 at the outlet of the stripper may also be used instead of the boiler water 17 as a cooling medium for cooling the vertical falling liquid film condenser I. This is efficient because the heating of the liquid at the outlet of the stripper in the decomposition step performed downstream of the apparatus for synthesizing urea can partially be performed along with the cooling of the vertical falling liquid film condenser I. For example, a line for directing the liquid at the outlet of the stripper to the shell side of the condenser I may be provided, and the heated liquid at the outlet of the stripper discharged from the shell side may be utilized in the downstream decomposition step.

EXAMPLES

Hereinafter, the present invention will be described more specifically with reference to Examples. However, the present invention is not intended to be limited to them.

Example 1

Table 1 shows a material balance, temperatures, and pressures in an example of urea production at 1725 t/day (t denotes a ton, i.e., 103 kg) with use of an apparatus for synthesizing urea having an embodiment shown in FIG. 1.

Of raw material ammonia 1 at a pressure of 23 MPaG and a temperature of 30° C., 39.7 t/hour were heated in a heat exchanger G to 140° C. and supplied from a line 1a to an ejector E, while 1.0 t/hour was supplied through a line 1b to a condenser B. On the other hand, carbon dioxide 2 at a pressure of 0.1 MPaG and a temperature of 40° C. was pressurized in a compressor H and thereby converted to carbon dioxide at a pressure of 16 MPaG and a temperature of 120° C. And 41.2 t/hour and 9.1 t/hour of this carbon dioxide were supplied through a line 2a to a stripper C and through a line 2b to a synthesis reactor A, respectively, to produce urea.

The supplied ammonia 1a in the ejector E was mixed with a synthesis solution 6 at a pressure of 15.2 MPaG from a gas-liquid separator F and supplied at a pressure of 15.5 MPaG from a line 8 to the synthesis reactor A having a synthesis zone.

The synthesis reactor A was operated at a pressure of 15.5 MPaG, at a temperature of 182° C., at N/C of 3.7, at H/C of 0.58, and with a residence time of 20 minutes to synthesize urea. The conversion ratio with respect to carbon dioxide in the synthesis reactor was 63%.

A urea-containing synthesis solution 4 from a down pipe located in the upper part of the synthesis reactor A was supplied to a stripper C. Medium-pressure steam 15 was supplied to the shell side of the stripper C and discharged therefrom as condensed water 16 after supplying heat for the decomposition of carbamate. On the tube side of the stripper C, the decomposition of carbamate and stripping were performed at an upper part temperature of 184° C. and lower part temperature of 171° C. and at a pressure of 15.5 MPaG to thereby separate gaseous components in the upper part. The gaseous components 5 were sent to the condenser B, and a synthesis solution 10 coming out of the bottom of the stripper C was sent to a decomposition apparatus.

Example 4

The same study as in Example 1 was conducted except that an apparatus for synthesizing urea having an embodiment shown in FIG. 4 was used. Results such as a material balance were obtained as shown in Table 1, as with Example 1.

Example 5

A study was conducted on an example of urea production at 1725 tons/day with use of an apparatus for synthesizing urea having an embodiment shown in FIG. 5. In the embodiment shown in FIG. 5, gaseous components coming out of a stripper C were partially condensed in a vertical shell and tube falling liquid film condenser I and then sent to a condenser B. Boiler water 17 was supplied to the shell side of the vertical falling liquid film condenser, in which the boiler water 17 was partially converted by heat recovery to low-pressure steam and discharged as a mixed-phase flow of the boiler water and the low-pressure steam from a line 18. Supplying conditions for raw material ammonia and raw material carbon dioxide and operating conditions for the synthesis reactor A, the condenser B, and the stripper C were the same as in Example 1. Results such as a material balance were obtained as shown in Table 1, as with Example 1.

TABLE 1

|  |  | Line No. | | | | | | | | | | | | |
| --- | --- | --- | --- | --- | --- | --- | --- | --- | --- | --- | --- | --- | --- | --- |
|  |  | 1 | 1a | 1b | 2 | 2a | 2b | 2c | 4 | 5 | 6 | 8 | 10 | 11 | 12 |
| Urea | t/h |  |  |  |  |  |  |  | 77.3 |  | 50.8 | 50.8 | 73.5 | 0.3 |  |
| Ammonia | t/h | 40.7 | 39.7 | 1.0 |  |  |  |  | 86.9 | 69.7 | 62.3 | 102.0 | 19.2 | 21.9 | 1.6 |
| Carbon Dioxide | t/h |  |  |  | 52.7 | 41.2 | 9.1 | 2.4 | 33.6 | 58.5 | 43.9 | 43.9 | 18.9 | 24.7 | 2.2 |
| Water | t/h |  |  |  |  |  |  |  | 44.6 | 6.4 | 36.7 | 36.7 | 37.2 | 15.3 | 0.2 |
| Total | t/h | 40.7 | 39.7 | 1.0 | 52.7 | 41.2 | 9.1 | 2.4 | 242.4 | 134.6 | 193.7 | 233.4 | 148.8 | 62.2 | 4.0 |
| Temperature | ° C. | 30 | 140 | 30 | 40 | 120 | 120 | 150 | 182 | 184 | 180 | 170 | 171 | 105 | 160 |
| Pressure | MPaG | 23.0 | 23.0 | 23.0 | 0.1 | 16.0 | 16.0 | 0.5 | 15.5 | 15.5 | 15.2 | 15.5 | 15.5 | 16.0 | 15.2 |
| N/C | mol/mol |  |  |  |  |  |  |  | 3.7 |  | 2.9 |  |  |  |  |
| H/C | mol/mol |  |  |  |  |  |  |  | 0.58 |  | 0.65 |  |  |  |  |
| CO2 conversion ratio | % |  |  |  |  |  |  |  | 63 |  | 46 |  |  |  |  |

The gaseous components at 134.6 t/hour (line 5) from the stripper C and the recycled carbamate liquid at 62.2 t/hour (line 11) were sent to the condenser. The condenser was operated at a temperature of 180° C., at a pressure of 15.2 MPaG, at N/C of 2.9, at H/C of 0.65, and with a residence time of 20 minutes to synthesize urea and so on. The conversion ratio with respect to carbon dioxide in the condenser was 46%.

Example 2

The same study as in Example 1 was conducted except that an apparatus for synthesizing urea having an embodiment shown in FIG. 2 was used. Results such as a material balance were obtained as shown in Table 1, as with Example 1.

Example 3

The same study as in Example 1 was conducted except that an apparatus for synthesizing urea having an embodiment shown in FIG. 3 was used. Results such as a material balance were obtained as shown in Table 1, as with Example 1.

INDUSTRIAL APPLICABILITY

An apparatus for synthesizing urea of the present invention is suitably used in urea manufacture wherein urea is manufactured from ammonia and carbon dioxide. Moreover, a method for revamping an apparatus for synthesizing urea of the present invention is suitable for revamping an existing apparatus for synthesizing urea and thereby boosting production and improving efficiency.

The invention claimed is:

1. An apparatus for synthesizing urea comprising:
   a synthesis reactor for reacting ammonia with carbon dioxide to obtain a urea synthesis solution containing urea, unreacted ammonia, unreacted carbon dioxide and water;
   a stripper for stripping the urea synthesis solution with use of at least a part of raw material carbon dioxide to separate a gas mixture containing the unreacted ammonia and the unreacted carbon dioxide;
   a vertical submerged condenser having a shell and tube structure for condensing the gas mixture in an absorbing medium on the shell side while cooling the gas mixture with a cooling medium passing through the tube side; and recycling means for recycling a liquid obtained from the vertical submerged condenser to the synthesis reactor,
wherein the vertical submerged condenser is placed below the synthesis reactor.

2. The apparatus according to claim 1, wherein the recycling means comprises an ejector of which driving source is raw material ammonia.

3. The apparatus according to claim 1, wherein the synthesis reactor and the vertical submerged condenser are divided from each other and integrated with each other, and the synthesis reactor is placed above the vertical submerged condenser.

4. The apparatus according to claim 3, further comprising a scrubber for scrubbing a gas that has not been condensed in the vertical submerged condenser, wherein the scrubber is placed in the interior of the vertical submerged condenser.

5. The apparatus according to claim 1, further comprising a scrubber for scrubbing a gas that has not been condensed in the vertical submerged condenser, wherein the vertical submerged condenser and the scrubber are integrated with each other.

6. The apparatus according to claim 5, wherein the scrubber is placed in the interior of the vertical submerged condenser.

7. The apparatus according to claim 5, wherein the synthesis reactor is a horizontal type.

8. A method for revamping an existing apparatus for synthesizing urea having a synthesis reactor for reacting ammonia with carbon dioxide to obtain a urea synthesis solution containing urea, unreacted ammonia, unreacted carbon dioxide and water, comprising:
installing the apparatus with:
a stripper for stripping the urea synthesis solution with use of at least a part of raw material carbon dioxide to separate a gas mixture containing the unreacted ammonia and the unreacted carbon dioxide;
a vertical submerged condenser having a shell and tube structure for condensing the gas mixture in an absorbing medium on the shell side while cooling the gas mixture with a cooling medium passing through the tube side; and
recycling means for recycling a liquid obtained from the vertical submerged condenser to the synthesis reactor,
wherein the vertical submerged condenser is placed below the synthesis reactor.

9. A method for revamping an existing apparatus for synthesizing urea having
a synthesis reactor for reacting ammonia with carbon dioxide to obtain a urea synthesis solution containing urea, unreacted ammonia, unreacted carbon dioxide and water;
a stripper for stripping the urea synthesis solution with use of at least a part of raw material carbon dioxide to separate a gas mixture containing the unreacted ammonia and the unreacted carbon dioxide; and
a vertical falling liquid film condenser for condensing the gas mixture; comprising installing the apparatus with:
a vertical submerged condenser having a shell and tube structure for condensing the gas mixture in an absorbing medium on the shell side while cooling the gas mixture with a cooling medium passing through the tube side; and
recycling means for recycling a liquid obtained from the vertical submerged condenser to the synthesis reactor,
wherein the vertical submerged condenser is placed below the synthesis reactor.

10. The revamping method according to claim 9, wherein the vertical falling liquid film condenser comprises cooling means, and
the method further comprises providing the apparatus with a line for directing a liquid at the outlet of the stripper to the cooling means.

11. The apparatus according to claim 2, wherein the synthesis reactor and the vertical submerged condenser are divided from each other and integrated with each other, and the synthesis reactor is placed above the vertical submerged condenser.

12. The apparatus according to claim 11, further comprising a scrubber for scrubbing a gas that has not been condensed in the vertical submerged condenser, wherein the scrubber is placed in the interior of the vertical submerged condenser.

13. The apparatus according to claim 2, further comprising a scrubber for scrubbing a gas that has not been condensed in the vertical submerged condenser, wherein the vertical submerged condenser and the scrubber are integrated with each other.

14. The apparatus according to claim 13, wherein the scrubber is placed in the interior of the vertical submerged condenser.

15. The apparatus according to claim 6, wherein the synthesis reactor is a horizontal type.

16. The apparatus according to claim 13, wherein the synthesis reactor is a horizontal type.

17. The apparatus according to claim 14, wherein the synthesis reactor is a horizontal type.

18. A method for synthesizing urea using an apparatus having a synthesis reactor for reacting ammonia with carbon dioxide to obtain a urea synthesis solution containing urea, unreacted ammonia, unreacted carbon dioxide and water, comprising:
stripping by a stripper the urea synthesis solution with use of at least a part of raw material carbon dioxide to separate a gas mixture containing the unreacted ammonia and the unreacted carbon dioxide;
condensing by a vertical submerged condenser having a shell and tube structure, the gas mixture in an absorbing medium on the shell side while cooling the gas mixture with a cooling medium passing through the tube side; and
recycling a liquid obtained from the vertical submerged condenser to the synthesis reactor,
wherein the vertical submerged condenser is placed below the synthesis reactor.

* * * * *